United States Patent [19]

Lukacs, III

[11] Patent Number: 5,039,636

[45] Date of Patent: Aug. 13, 1991

[54] PREPARATION OF ALUMINUM TITANATE FROM AN ORGANOMETALLIC OLIGOMER

[75] Inventor: Alexander Lukacs, III, Wilmington, Del.

[73] Assignee: Hercules Incorporated, Wilmington, Del.

[21] Appl. No.: 571,046

[22] Filed: Aug. 10, 1990

[51] Int. Cl.$^5$ .............................................. C04B 35/46
[52] U.S. Cl. .................................... 501/134; 501/153; 556/27; 556/31
[58] Field of Search .................... 556/27, 31; 501/134, 501/153

[56] References Cited

U.S. PATENT DOCUMENTS

| | | | |
|---|---|---|---|
| 3,825,653 | 7/1974 | Duerksen et al. | 423/598 |
| 3,950,460 | 4/1976 | Mastrangelo et al. | 264/44 |
| 4,159,209 | 6/1979 | Womersley | 106/308 N |
| 4,332,844 | 6/1982 | Hamada et al. | 427/387 |
| 4,333,881 | 6/1982 | Greco et al. | 260/429 R |
| 4,434,103 | 2/1984 | Interrante | 260/448 |
| 4,460,654 | 7/1984 | Interrante | 428/428 |
| 4,483,944 | 11/1984 | Day et al. | 502/439 |
| 4,554,186 | 11/1985 | Williams | 427/387 |
| 4,720,562 | 1/1988 | Malpass et al. | 556/27 |

OTHER PUBLICATIONS

O. Yamguchi et al., The Science and Engineering Review of Dashisha University, 22 (1), Apr. 1981, 26.

*Primary Examiner*—William R. Dixon, Jr.
*Assistant Examiner*—Alan Wright
*Attorney, Agent, or Firm*—Joanne W. Patterson

[57] ABSTRACT

An aluminum- and titanium-containing oligomer is prepared by a controlled hydrolysis reaction between a chelated aluminum compound and an organotitanium compound. The oligomer is heated to 800° C. in an oxygen-containing atmosphere to produce β-aluminum titanate.

6 Claims, No Drawings

PREPARATION OF ALUMINUM TITANATE FROM AN ORGANOMETALLIC OLIGOMER

FIELD OF THE INVENTION

This invention relates to the preparation of aluminum titanate. This invention particularly relates to the preparation of β-aluminum titanate by pyrolysis of an aluminum- and titanium-containing oligomer.

BACKGROUND OF THE INVENTION

Aluminum titanate ($Al_2TiO_5$) ceramic is suitable for use as an insulative coating for metals, for applications where junctures between two materials of widely different thermal expansion coefficients are encountered and in applications such as catalyst supports where porous structures having good thermal shock properties are needed. It exhibits a unique combination of a high melting point (1860° C.), and low coefficient of thermal expansion ($0.5 \times 10^{-6}$/°C. over a temperature range of 20° C. to 1000° C.).

The traditional method for preparing aluminum titanate is to mix $Al_2O_3$ and $TiO_2$ and heat to a temperature of 1300° to 1400° C. Other methods for preparing aluminum titanate have also been described. For example, U.S. Pat. No. 3,825,653 describes a method for preparing a sinterable aluminum titanate powder by (1) coprecipitating halides or alkoxides of aluminum and titanium as a solid hydroxide, (2) drying the resulting hydrated aluminum titanium hydroxide and (3) calcining in air at 700°-800° C. In *The Science and Engineering Review of Doshisha University,* 22 (1), April 1981, p. 26, Yamaguchi et al. describe the preparation of β-aluminum titanate at a temperature of 1320° C. using a mixture of α-$Al_2O_3$ and $TiO_2$ powders. The powder mixture was obtained by the simultaneous hydrolysis of aluminum and titanium alkoxides to give an equimolar mixture of the amorphous oxides.

SUMMARY OF THE INVENTION

A process has now been found for making liquid precursors that can be converted to β-aluminum titanate at considerably lower temperatures than those used for the preparation of $Al_2TiO_5$ from $Al_2O_3$ and $TiO_2$.

The oligomer of the present invention has the formula

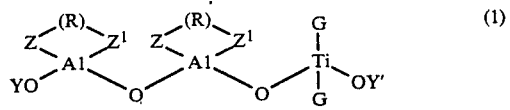
(1)

where R is a divalent organic radical, Z and $Z^1$ can be the same or different and are selected from —O—, —N= and —S—; Y and Y' can be the same or different and are selected from substituted or unsubstituted 1-13 carbon hydrocarbon radicals and G is OY', $R^1$, $R^2$ or

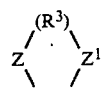

where $R^1$ and $R^2$ can be the same or different and are selected from alkylpsubstituted or unsubstituted cyclopentadienide ligands and $R^3$ is a divalent organic radical that can be the same as R or different. A process for preparing the oligomer as well as a process for converting the oligomer to β-aluminum titanate are also disclosed.

DETAILED DESCRIPTION OF THE INVENTION

The oligomers of this invention are prepared by a controlled hydrolysis reaction in which two equivalents of a chelated aluminum compound having the formula

(2)

are reacted with one equivalent of water to form a dimer. One equivalent of the dimer is then stirred at room temperature for a short period of time, typically 30 minutes, with one equivalent of a titanium compound having the formula $Ti(OH')_4$ or

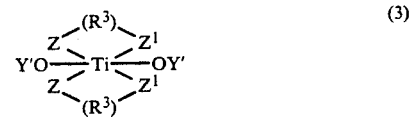
(3)

or

(4)

in a hydrocarbon solvent such as benzene toluene or cyclohexane, and one equivalent of water. The solvent is then stripped off. Y, Y', R, Z, $Z^1$, $R^1$, $R^2$ and $R^3$ have the meaning described above.

In the formula for the chelated aluminum compound (2), —Z—(R)—$Z^1$— can be, for example, dithio acetylacetonato, ethyl malonato, ethyl acetoacetato, acetylacetonato and 3-ethyl acetylacetonato. The radical —OY can be, for example, methoxy, ethoxy, isopropoxy or 2-methoxyethoxy. Suitable substituents for Y include, for example, halides, alkoxy, aryloxy and nitro groups. Specific examples of such aluminum compounds include, for example, (acetylacetonato)aluminum diisopropoxide, (ethyl acetoacetato)aluminum diisopropoxide, (ethyl malonato)aluminum diethoxide and (acetylacetonato)aluminum bis(2-methoxyethoxide).

Examples of the chelated titanium compounds (3) that can be used in the reaction include, for example, bis(acetylacetonato)titanium diisopropoxide and bis-(ethyl acetoacetato)-titanium diethoxide.

In the formulas for the titanium compounds (4), the cyclopentadienide radicals can be, for example, cyclopentadienide, pentamethylcyclopentadienide and methylcyclopentadienide. Specific examples of such compounds include, for example, bis(cyclopentadienyl)titanium diisopropoxide and bis(pentamethylcyclopentadienyl)titanium diethoxide.

The aluminum- and titanium-containing oligomer is a viscous liquid that is soluble in aromatic hydrocarbon solvents such as toluene and xylene, as well as in hexane and higher alkanes.

The oligomer can be pyrolyzed to yield β-aluminum titanate by heating in an inert or oxygen-containing atmosphere to 800° C. Conversion at this temperature is a significant improvement over traditional methods for preparing aluminum titanate, since the onset of formation of β-aluminum titanate from Al₂O₃ and TiO₂ is typically in excess of 1300° C.

Since β-aluminum titanate undergoes a eutectoid-like decomposition at 800°–1300° C. to form rutile and corundum, a small amount of "stabilizer" must be added in order to sinter the ceramic. Rare earth oxides such as lanthanum oxide or neodymium oxide, as well as alkaline earth metal oxides, can be used as the stabilizer. Sintering can be accomplished at a temperature of 1300°–1800° C., preferably at about 1500° C., by initially pyrolyzing to about 1,000° C. under argon or one of the other noble gases, and then heating to the sintering temperature in an oxygen-containing atmosphere such as air. The organic portion of the oligomer is burned out during sintering, resulting in the evolution of volatiles. If no sintering aid is added, a porous product is formed. If a dense ceramic is desired, a sintering aid such as MgO, CaO, MnO₂, Fe₂O₃, Y₂O₃, La₂O₃, Nd₂O₃, ZrSiO₄, SnO₂, ZnO₂ or SiO₂ can be added before sintering. Mullite can optionally be mixed with the aluminum titanate before sintering to increase the strength of the sintered product while retaining low thermal expansion characteristics.

Porous, honeycombed bulk ceramics can be formed from the oligomers of this invention. Since the oligomers are soluble in hydrocarbon solvents, ceramic fibers and coatings can also be formed. The unique properties exhibited by β-Al₂TiO₅ make it suitable for use in such specialized applications as exhaust/intake ports and manifolds for ceramic engines and catalytic converter supports for automobiles, all of which require not only a high melting point, but a porous structure and a low coefficient of thermal expansion.

EXAMPLE 1

Preparation of (Ethylacetoacetato) Aluminum Diisopropoxide

A solution of aluminum isopropoxide (408.5 g, 2.0 moles) in distilled cyclohexane (1000 ml) is stirred at room temperature for one hour.

Distilled ethyl acetoacetate (255 ml, 2.0 moles) is added dropwise over a two hour period. During the addition the mixture is kept cold in an ice bath. After the addition is complete, the ice bath is removed and the pale yellow solution is stirred at room temperature overnight under nitrogen.

The solution is centrifuged to remove any unreacted solids and stripped of solvent. The crude product is vacuum distilled (boiling point=160° C., 6 mm) to yield 457.0 g of a clear yellow viscous oil (83% yield). The product is identified by elemental analysis and ¹H NMR.

EXAMPLE 2

Hydrolysis of (Ethylacetoacetato)aluminum Diisopropoxide

To a solution of (ethylacetoacetato)aluminum diisopropoxide (455 g, 1.66 moles) in distilled cyclohexane (769 ml) is added dropwise a solution of distilled isopropanol (186 ml) and water (14.94 g, 0.83 moles). The solution is stirred under nitrogen at room temperature for one hour. Solvent is removed by distillation at ambient pressure. The residue is then subjected to a high vacuum until all residual solvent has been removed. A pale yellow viscous oil (402.2 g) is recovered at greater than 100% yield. The aluminum-containing dimer is identified by elemental analysis and ¹H NMR.

EXAMPLE 3

Preparation of Aluminum-Titanium Oligomer

A solution of distilled isopropanol (680 ml) and water (16.2 g, 0.9 moles) is added dropwise to a solution of the aluminum-containing dimer (400 g, 0.90 moles) prepared as described in Example 2, and titanium(diisopropoxide)bis(2,4-pentanedionate) (436.8 g, 0.90 moles at a 75% solution in isopropanol) in freshly distilled cyclohexane (680 ml). The reaction mixture is stirred for one hour at room temperature under nitrogen. Solvent is removed by distillation at ambient pressure and the residue subjected to a high vacuum until all traces of solvent have been removed. The reaction yielded 568.8 g of an orange waxy solid (92% yield) soluble in nonpolar organic solvents. The product is identified by elemental analysis and ¹H NMR and has the following structure:

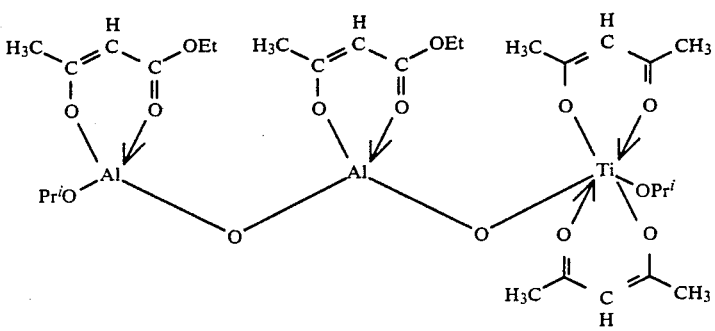

where Pr$^i$ is isopropyl and Et is ethyl.

EXAMPLE 4

Pyrolysis of Aluminum-Titanium Oligomer

The aluminum-titanium oligomer prepared as described in Example 3 is slowly heated in air on gold foil in a small muffle furnace to a temperature of 800° C. and held at this temperature for one hour. The X-ray diffraction pattern of the white crystalline product indicated the formation of β-aluminum titanate.

EXAMPLE 5

Preparation of a Mullite/B-aluminum Titanate Ceramic

Ten grams of the oligomer prepared as described in Example 3 are dissolved in 120 ml of toluene. To this mixture are added 30 g of mullite, 45 g TiO₂, 23 g Al₂O₃, 1.09 g Fe₂O₃, 1.32 g La₂O₃, and 0.44 g Nd₂O₃. After thoroughly dispersing the powders in the solution by mixing, the toluene solvent is removed under vacuum. The resulting powder (6.04 g) is then sieved through a 325 mesh screen and dry pressed into a 6.37 cm×1.28 cm×0.31 cm bar (2.38 g/cm³ green density) using a Carver press. The bar is sintered by heating from ambient temperature to 1,000° C. at 350° C./hour under argon, holding at that temperature for two hours, and then heating from 1,000° C. to 1,500° C. at a rate of 250° C./hour in air. The bar is held at 1,500° C. for six hours before cooling to room temperature. The bar exhibits a 5.79% net weight loss during firing (9.5% linear shrinkage) and a fired density of 3.04 g/cm³. The flexural strength of the sample is 1814 psi as measured with an Instron 1125 tester using a four point bend test equipped with a 500 kg reversible load cell.

What I claim and desired to protect by Letters Patent is:

1. An oligomer having the formula

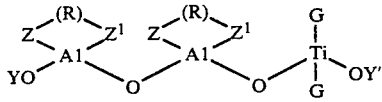

where R is a divalent organic radical, Z and $Z^1$ can be the same or different and are selected from —O—, —N= and —S—; Y and Y' can be the same or different and are selected from substituted or unsubstituted 1–13 carbon monovalent hydrocarbon radicals and G is OY', $R^1$, $R^2$ or

where $R^1$ and $R^2$ can be the same or different and are selected from alkyl-substituted or unsubstituted cyclopentadienide ligands and $R^3$ is divalent organic radical that can be the same as R or different.

2. The oligomer of claim 1 wherein Y and Y' are isopropyl, —Z—(R)—$Z^1$— is an ethylacetoacetato group and G is a pentanedionate group.

3. A process for preparing the oligomer of claim 1 by (1) reacting two equivalents of an aluminum compound having the formula

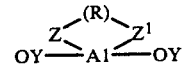

with one equivalent of water to form a dimer, (2) reacting one equivalent of the dimer with one equivalent of a titanium compound having the formula (a) Ti(OY')$_4$, (b) 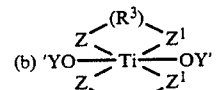 (3)

or (c) 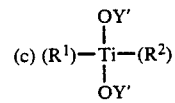

in a hydrocarbon solvent, and on equivalent of water and (4) stripping off the solvent.

4. The process of claim 3 wherein the aluminum compound is (ethylacetoacetato) aluminum diisopropoxide and the titanium compound is titanium (diisopropoxide) bis(2,4-pentanedionate).

5. A process for preparing β-aluminum titanate by heating the oligomer of claim 1 to a temperature of about 800° C.

6. A process for preparing β-aluminum titanate by heating the oligomer of claim 2 to a temperature of about 800° C. in an oxygen-containing atmosphere.

* * * * *

UNITED STATES PATENT AND TRADEMARK OFFICE
CERTIFICATE OF CORRECTION

PATENT NO. : 5,039,636

DATED : August 13, 1991

INVENTOR(S) : Alexander Lukacs, III

It is certified that error appears in the above-identified patent and that said Letters Patent is hereby corrected as shown below:

Col. 1, line 65 "alkylpsubstituted" should be deleted and replaced by -- alkyl-substituted --.

Col. 2, line 18 "$Ti(OH')_4$" should be deleted and replaced by -- $Ti(OY')_4$ --.

Col. 3, line 54, "A solution of a luminum" should be deleted and replaced by -- A solution of aluminum --.

Col. 4, line 23, "Example 2, and" should be deleted and replaced by -- Example 2 and --.

Col. 5, line 30, "$r^2$" should be deleted and replaced by -- $R^2$ --.

Col. 6, line 29 "on" should be deleted and replaced by -- one --.

Signed and Sealed this

Twenty-ninth Day of December, 1992

*Attest:*

DOUGLAS B. COMER

*Attesting Officer*     *Acting Commissioner of Patents and Trademarks*